United States Patent
Tiitta et al.

(10) Patent No.: US 12,187,965 B2
(45) Date of Patent: Jan. 7, 2025

(54) PROCESS FOR INTEGRATED PRODUCTION OF RENEWABLE FUELS AND CHEMICALS

(71) Applicant: Neste Oyj, Espoo (FI)

(72) Inventors: Marja Tiitta, Porvoo (FI); Jukka Myllyoja, Porvoo (FI); Väinö Sippola, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 17/418,362

(22) PCT Filed: Dec. 20, 2019

(86) PCT No.: PCT/FI2019/050915
§ 371 (c)(1),
(2) Date: Jun. 25, 2021

(87) PCT Pub. No.: WO2020/141255
PCT Pub. Date: Jul. 9, 2020

(65) Prior Publication Data
US 2022/0041939 A1     Feb. 10, 2022

(30) Foreign Application Priority Data

Dec. 31, 2018 (FI) ..................... 20186144
Dec. 31, 2018 (FI) ..................... 20186145
Dec. 31, 2018 (FI) ..................... 20186146

(51) Int. Cl.
*C10G 3/00* (2006.01)
*C07C 29/09* (2006.01)
(Continued)

(52) U.S. Cl.
CPC .............. *C10G 3/48* (2013.01); *C07C 29/095* (2013.01); *C10G 3/50* (2013.01); *C10G 7/06* (2013.01);
(Continued)

(58) Field of Classification Search
CPC ... C10G 3/48; C10G 3/50; C10G 7/06; C10G 45/64; C10G 65/02; C10G 2300/1007;
(Continued)

(56) References Cited

U.S. PATENT DOCUMENTS

| | | | |
|---|---|---|---|
| 2,495,071 A | 1/1950 | Victor | |
| 2003/0057133 A1* | 3/2003 | Benazzi ................ | C10G 69/14 208/57 |

(Continued)

FOREIGN PATENT DOCUMENTS

| | | |
|---|---|---|
| CN | 107673952 A | 2/2018 |
| CN | 108325535 A | 7/2018 |

(Continued)

OTHER PUBLICATIONS

Finnish Search Report dated Apr. 26, 2019, issued by the Finnish Patent and Registration Office in the corresponding Finnish Patent Application No. 20186146. (10 pages).

(Continued)

*Primary Examiner* — Michelle Stein
(74) *Attorney, Agent, or Firm* — Buchanan Ingersoll & Rooney PC

(57) ABSTRACT

The present disclosure provides a versatile process for producing valuable renewable hydrocarbons from triglyceride containing feedstock. The triglyceride containing feedstock is first split to provide a mixture containing fatty acids, glycerol and water, from which a phase separation provides an oily phase, and an aqueous phase. The oily phase containing fatty acids is subjected to fractionation, whereby specific fractions may be refined to products with controlled hydroprocessing. Products may contain paraffinic renewable aviation fuel components, paraffinic renewable base oil, renewable paraffinic diesel fuel components, renewable paraffinic technical fluid, or any combination thereof.

30 Claims, 2 Drawing Sheets

(51) Int. Cl.
*C10G 7/06* (2006.01)
*C10G 45/64* (2006.01)
*C10G 65/02* (2006.01)
*C10G 65/14* (2006.01)

(52) U.S. Cl.
CPC ............ *C10G 45/64* (2013.01); *C10G 65/02* (2013.01); *C10G 65/14* (2013.01); *C10G 2300/1007* (2013.01); *C10G 2300/1011* (2013.01); *C10G 2300/4006* (2013.01); *C10G 2300/4012* (2013.01); *C10G 2300/4018* (2013.01); *C10G 2400/04* (2013.01); *C10G 2400/08* (2013.01)

(58) Field of Classification Search
CPC .... C10G 2300/1011; C10G 2300/1014; C10G 2300/1018; C10G 2300/01; C10G 2400/04; C10G 2400/08; C10G 2400/10; C10G 2400/12; C10G 2400/14; C10G 65/14–18
See application file for complete search history.

(56) References Cited

U.S. PATENT DOCUMENTS

| | | | | |
|---|---|---|---|---|
| 2007/0010682 | A1* | 1/2007 | Myllyoja | C10G 45/02 554/174 |
| 2007/0161832 | A1* | 7/2007 | Myllyoja | C10M 105/04 585/7 |
| 2007/0260102 | A1* | 11/2007 | Duarte Santiago | C10G 45/00 585/733 |
| 2009/0005614 | A1* | 1/2009 | Hulteberg | C07C 29/175 568/903 |
| 2009/0049739 | A1 | 2/2009 | Morgan | |
| 2009/0069610 | A1* | 3/2009 | Roberts, IV | C10G 45/68 585/24 |
| 2009/0088351 | A1* | 4/2009 | Miller | C11C 3/006 508/216 |
| 2010/0326387 | A1* | 12/2010 | Yeh | F02B 1/12 123/1 A |
| 2011/0107656 | A1* | 5/2011 | Miller | C10G 57/02 44/307 |
| 2011/0155631 | A1* | 6/2011 | Knuuttila | C10G 1/00 208/15 |
| 2012/0083633 | A1* | 4/2012 | Aulich | C10G 3/45 585/240 |
| 2012/0209041 | A1* | 8/2012 | Hanks | C10G 47/36 585/250 |
| 2013/0310620 | A1* | 11/2013 | Kalnes | C10G 3/47 585/733 |
| 2014/0171700 | A1* | 6/2014 | Roberts | C10M 109/02 585/17 |
| 2015/0018588 | A1* | 1/2015 | Myllyoja | B01J 23/8872 585/310 |
| 2015/0027925 | A1* | 1/2015 | Joseck | C10M 101/02 208/80 |
| 2017/0362154 | A1* | 12/2017 | Kettunen | B01J 23/883 |

FOREIGN PATENT DOCUMENTS

| | | | |
|---|---|---|---|
| DE | 102008026583 A1 | 12/2009 | |
| EP | 1741768 A1 | 1/2007 | |
| EP | 2253608 A1 * | 11/2010 | ............... C10G 3/50 |
| EP | 2155838 B1 | 9/2014 | |
| EP | 3012310 A1 | 4/2016 | |
| EP | 3184611 A1 | 6/2017 | |
| FI | 100248 B | 10/1997 | |
| WO | 2007068795 A1 | 6/2007 | |
| WO | 2007068799 A2 | 6/2007 | |
| WO | 2014128227 A1 | 8/2014 | |
| WO | 2015142887 A1 | 9/2015 | |
| WO | 2015181721 A1 | 12/2015 | |
| WO | 2016062868 A1 | 4/2016 | |
| WO | 2018020321 A1 | 2/2018 | |
| WO | 2018193074 A1 | 10/2018 | |
| WO | WO-2018234187 A1 * | 12/2018 | ............... C10G 3/49 |

OTHER PUBLICATIONS

Finnish Search Report dated Apr. 29, 2019, issued by the Finnish Patent and Registration Office in the corresponding Finnish Patent Application No. 20186114. (7 pages).

Finnish Search Report dated Apr. 29, 2019, issued by the Finnish Patent and Registration Office in the corresponding Finnish Patent Application No. 20186145. (8 pages).

International Search Report (PCT/ISA/210) and Written Opinion (PCT/ISA/237) mailed on Feb. 13, 2020, by the European Patent Office as the International Searching Authority for International Application No. PCT/FI2019/050915.

Notification of Transmittal of The International Preliminary Report on Patentability (PCT Rule 71.1) (Form PCT/IPEA/416), International Preliminary Report on Patentability (PCT Article 36 and Rule 70) (Form PCT/IPEA/409) issued on Mar. 22, 2021, in the corresponding International Application No. PCT/FI2019/050915. (9 pages).

Alm, Martin, "Animal fats" (2013), [online]. Available at http://lipidlibrary.aocs.org/OilsFats/content.cfm?ItemNumber=40320 [Accessed Dec. 21, 2018].

Lin, X. et al., "Hydrogenolysis of Glyverol By the Combined Use of Zeolite and $Ni/Al_2O_3$ as Catalysts: A Route for Achieving High Selectivity to 1-Propanol", Energy&Fuels, vol. 28, pp. 3345-3351, Apr. 17, 2014.

Sun, D. et al., "Glycerol hydrogenolysis into useful C3 chemicals", Applied Catalysis B: Environmental 193, pp. 75-92, 2016.

Van Ryneveld, E. et al., "A catalytic route to lower alcohols from glycerol using Ni-supported catalysts", Green Chemistry, vol. 13, pp. 1819-1827, 2011.

Zhu, S. et al., "One-step hydrogenolysis of glycerol to biopropanols over $Pt-H_4SiW_{12}O_{40}/ZrO_2$ catalysts †", Green Chemistry, vol. 14, pp. 2607-2616, 2012.

* cited by examiner

PROCESS FOR INTEGRATED PRODUCTION OF RENEWABLE FUELS AND CHEMICALS

FIELD OF INVENTION

The present process for producing renewable hydrocarbon components is related to the field of utilization and processing of triglyceride containing feedstocks. According to an embodiment, the integrated production encompasses production of at least one fuel component and a renewable base oil or a renewable technical fluid, more specifically a renewable transformer oil.

BACKGROUND

Renewable or at least partly renewable transport fuels, such as biodiesel and renewable paraffinic diesel are currently available in the market. There is a growing end user demand for sustainable, renewable and recycled alternatives in the neighboring fields of aviation fuels, renewable base oil and technical fluid. Although not yet mandated to contain renewable products, there are clear signs of legislative directives emerging also for these areas. Currently, there is limited offering of renewable alternatives available for the above mentioned applications. Further, the renewable alternatives are typically not price competitive with the conventional offering, which has limited the development of the renewable and recycled aviation fuels and technical fluid.

One field of interest for renewable chemicals are technical fluids. An example of technical fluids is transformer oil or insulating oil, which is an oil that is stable at high temperatures and has excellent electrical insulating properties. Transformer oil's primary functions are to insulate and cool a transformer. It must therefore have high dielectric strength, thermal conductivity, and chemical stability, and must keep these properties when held at high temperatures for extended periods. Typical specifications for transformer oil are: flash point 140° C. or greater, pour point −30° C. or lower, dielectric breakdown voltage 28 kV (RMS) or greater.

There is a need to develop feasible processes in these areas. In transformer oil segment, there is a clear end-user need to develop solutions that offer improved thermal transfer characteristics, which would enable smaller transformer installations. Lower viscosity of the transformer oil would be beneficial to achieve this target. Further, biological origin of the feedstock is requested by the end users.

Renewable resources and bio-based feedstocks present a sustainable alternative to petrochemical sources. The feedstock has been derived from e.g. variety of vegetable oils, animal fats, recycled waste oils and even microbial oils. Hydrogenated vegetable oils such as palm oil, derivatives thereof, animal fat and other wastes or residues have been the major feedstock dominating the global renewable fuel market. In addition to fuels, fats and oils can be step-by-step processed also into renewable chemicals and renewable base oil. However, prevailing production processes rely on hydroprocessing of the feedstock as such producing a variety of products needing a fractionating distillation for recovery of products meeting specifications set by authorities. Hence, there is a need for a more sophisticated treatment of triglyceride containing feedstocks for production of renewable fuels and chemicals.

WO2014128227 relates to the use of an electrical equipment comprising electrically insulating fluid containing isoparaffins derived from a renewable carbon source in an electrical equipment. The fluid has a flash point of at least 210° C. and comprises at least 70 wt-% of the isoparaffins.

WO2015142887 relates to renewable base oil dielectric fluids such as isoparaffinic hydrocarbon based fluids derived from hydrocarbon terpenes such as myrcene, ocimene and farnesene. The dielectric fluid or coolant for electrical apparatuses comprises renewable hydrocarbon base oil having a molecular weight greater than 300 g/mol and less than 595 g/mol.

SUMMARY OF INVENTION

Herein is provided a process for producing renewable hydrocarbon components from triglyceride containing feedstock. The process is defined by process steps comprising
a. hydrolyzing said triglyceride containing feedstock to provide a mixture comprising fatty acids, glycerol and water;
b. subjecting said mixture comprising fatty acids, glycerol and water to a phase separation to recover an oily phase comprising fatty acids, and an aqueous phase comprising glycerol and water;
c. subjecting said oily phase comprising fatty acids to fractionation to provide a first fatty acid fraction comprising at least 80%-wt of free fatty acids having a carbon chain length of C16 or less, of the total fraction weight, and a second fatty acid fraction comprising free fatty acids having a carbon chain length of at least C17;
d. subjecting said first fatty acid fraction to
   hydroprocessing to provide paraffinic renewable aviation fuel components, or
   ketonisation before hydroprocessing to provide paraffinic renewable base oil, or
   a combination thereof;
e. subjecting said second fatty acid fraction to hydroprocessing to provide
   renewable paraffinic diesel fuel components, or
   renewable paraffinic technical fluid, or
   a combination thereof;
f. recovery of renewable hydrocarbon components from steps d and e.

The present inventors have found that a fractionation step dividing the oily phase obtained after splitting and phase separation, into relatively homogenic fatty acid fractions, the processing of said fatty acid fractions can be adjusted in such precision that desired and high-quality products can be recovered directly from hydroprocessing without need for product distillation. Mere product stabilization is sufficient.

Further, the present process provides means for controlling the desired product distribution according to demand for specific products obtainable from triglyceride containing feedstock. Control through the step a., adjusting the degree of splitting, preferably by hydrolysis, has shown to be an interesting novel tool for steering the product range obtained.

In addition to steering by splitting step a., a further option is provided by step d. and processing selections made therein. When conducting step d. as hydroprocessing of said first fatty acid stream, the hydroprocessing conditions may be tailored and controlled specifically to this process input and thereby, a high-quality renewable aviation fuel, hydroprocessed esters and fatty acids (HEFA), obtained.

Alternatively, or in addition, the first fatty acid fraction or a part thereof in step d. may be subjected to ketonisation prior to hydroprocessing. This specific process provides a high-quality base oil.

The second fatty acid fraction may be subjected to hydroprocessing to provide either renewable paraffinic diesel fuel components, or renewable paraffinic technical fluid. Provision of one of said components as product from step e is preferred. However, as an embodiment a combination thereof may be obtained.

Hence, as one aspect, the present invention relates to combined production of at least two, possibly three or even four or more paraffinic hydrocarbon products, renewable paraffinic aviation fuel components, renewable paraffinic diesel fuel components, renewable paraffinic base oil and renewable paraffinic technical fluid, by specific hydrodeoxygenation and isomerization. The renewable paraffinic aviation fuel component is preferably a HEFA fuel component. The technical fluid is preferably a transformer oil.

As another specific embodiment of the present process, the process may further comprise subjecting the aqueous phase comprising glycerol from step b. to process for converting said glycerol to renewable propanols. The recovery of C3-selection originating from triglycerides provides additional process economy through production of a valuable renewable propanol gasoline component as renewable fuel oxygenate component contributing to octane number, for example in gasoline blends.

Consequently, herein is further provided a novel use of any of the processes discussed above for producing at least one product selected from renewable paraffinic base oil, renewable paraffinic diesel fuel component, renewable paraffinic naphtha component, renewable propanols, renewable paraffinic aviation fuel component, and renewable transformer oil.

BRIEF DESCRIPTION OF THE FIGURES

Embodiments of the present invention are illustrated with schematic figures, wherein.

DETAILED DESCRIPTION OF THE INVENTION

Figure 1:
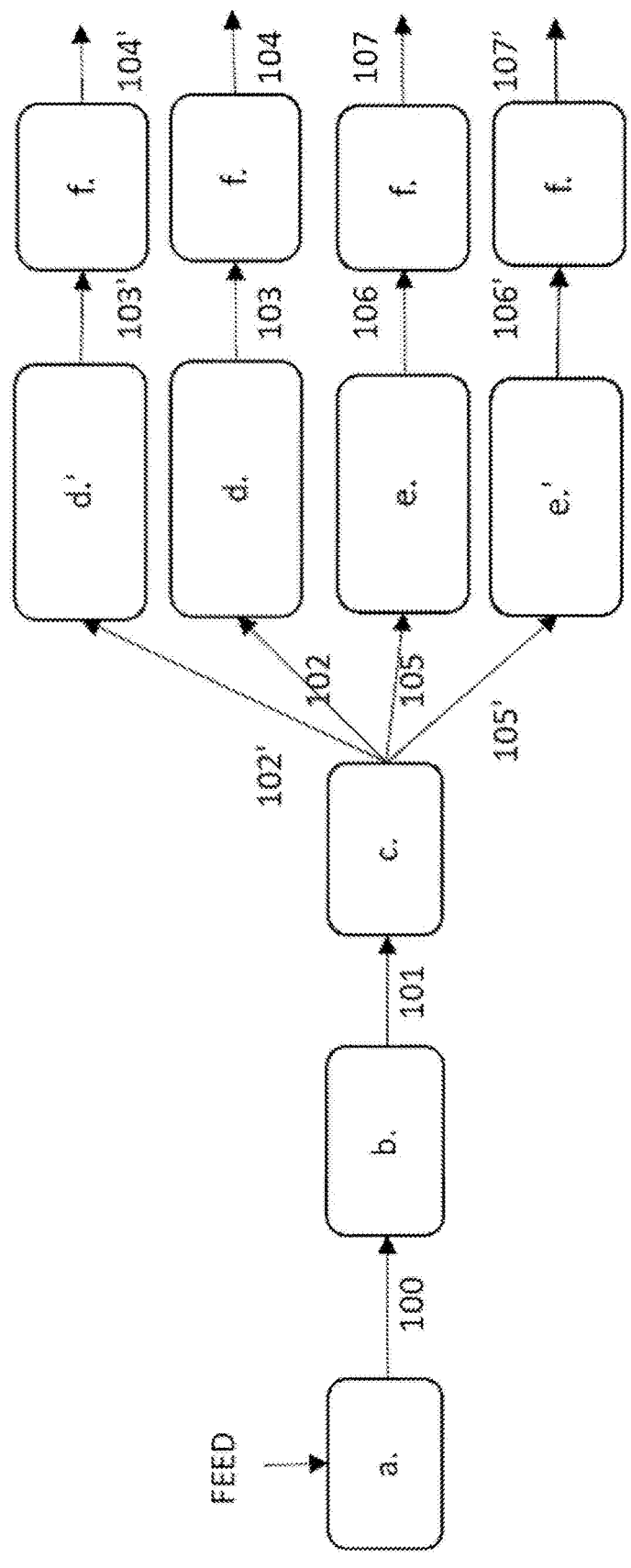
FIG. 1 shows the main steps of the present process with references to process steps claimed in a simplified manner.

In the present disclosure terminology used follows that generally known to a person skilled in the art. However, some of the processes and streams are defined in more detail.

A process for producing renewable hydrocarbon components from triglyceride containing feedstock, said process comprising a. hydrolyzing said triglyceride containing feedstock to provide a mixture comprising fatty acids, glycerol and water;
b. subjecting said mixture comprising fatty acids, glycerol and water to a phase separation to recover an oily phase comprising fatty acids, and an aqueous phase comprising glycerol and water;
c. subjecting said oily phase comprising fatty acids to fractionation to provide a first fatty acid fraction comprising at least 80%-wt of free fatty acids having a carbon chain length of C16 or less, of the total fraction weight, and a second fatty acid fraction comprising free fatty acids having a carbon chain length of at least C17;
d. subjecting said first fatty acid fraction to
   hydroprocessing to provide paraffinic renewable aviation fuel components, or
   ketonisation before hydroprocessing to provide paraffinic renewable base oil, or
   a combination thereof;
e. subjecting said second fatty acid fraction to hydroprocessing to provide
   renewable paraffinic diesel fuel components, or
   renewable paraffinic technical fluid, or
   a combination thereof;
f. recovery of renewable hydrocarbon components from steps d and e.

The Triglyceride Containing Feedstock

The triglyceride containing feedstock suitable for use in the process according to the present invention comprises free fatty acids and glycerides, at least 5%, preferably at least 50%, more preferably at least 80% by weight glycerides of the total triglyceride containing feedstock weight. Particularly suitable triglyceride containing feedstock for renewable paraffinic hydrocarbon components production and, especially, paraffinic renewable base oil production are those which comprise glycerides releasing abundantly C16 fatty acids in splitting, such as hydrolysis.

Several oils and fats contain significant amounts of C16 fatty acids (FA). Part of the fatty acids are already in the form of free fatty acids (FFA), but part are bound to glycerides as esters. Particularly preferable triglyceride containing feedstock for the present process comprises palm oil, animal fat or a combination thereof and more preferably palm oil waste materials, animal fat waste materials or a combination thereof.

Table 2 lists availability of C16 and C18 free fatty acids, and the fatty acid carbon chain lengths and unsaturation of exemplary fats and oils found in the literature, suitable for use in the process of the present invention.

TABLE 2

Exemplary glyceride feedstocks suitable for the process for producing renewable hydrocarbon components and optionally paraffinic renewable base oil of the present invention.

| | The fatty acid distribution of glyceride feedstocks suitable for the present process (%-wt) | | | | | | | | | | | | | Amount of FFAs [2]Amount of C16 and C18 |
|---|---|---|---|---|---|---|---|---|---|---|---|---|---|---|
| Fat/oil (%) | 8:0 | 10:0 | 12:0 | 14:0 | 16:0 | 18:0 | 18:1 | 18:2 | 18:3 | 20:0 | 20:1 | 22:0 | 22:1 | FFAs |
| Canola | | | | 0.1 | 4.1 | 1.8 | 60.9 | 21.0 | | 0.7 | | 0.3 | | |
| Cottonseed | | | | 0.7 | 21.6 | 2.6 | 18.6 | 54.4 | 0.7 | 0.3 | | 0.2 | | |
| Crumbe | | | | 1.7 | 0.8 | 16.1 | 8.2 | 2.9 | 3.3 | | | 2.2 | 59.5 | |
| Cuphea (PSR-23) | 0.8 | 81.9 | 3.2 | 4.3 | 3.7 | 0.3 | 3.6 | 2.0 | 0.3 | | | | | |
| Jatropha | | | | | [1]15 | | | | | | | | | [1]1.5-5 |

TABLE 2-continued

Exemplary glyceride feedstocks suitable for the process for producing renewable hydrocarbon components and optionally paraffinic renewable base oil of the present invention.

| | The fatty acid distribution of glyceride feedstocks suitable for the present process (%-wt) | | | | | | | | | | | | | Amount of FFAs [2]Amount of C16 and C18 |
|---|---|---|---|---|---|---|---|---|---|---|---|---|---|---|
| Fat/oil (%) | 8:0 | 10:0 | 12:0 | 14:0 | 16:0 | 18:0 | 18:1 | 18:2 | 18:3 | 20:0 | 20:1 | 22:0 | 22:1 | FFAs |
| Palm | | | 0.2 | 1.1 | 44.0 | 4.5 | 39.1 | 10.1 | 0.4 | 0.4 | | | | [1]4-7 |
| Palm Kernel | 3.3 | 3.4 | 48.2 | 16.2 | 8.4 | 2.5 | 15.3 | 2.3 | | 0.1 | 0.1 | | | |
| Palm stearin | | | | | [1]60 | | | | | | | | | [1]0.1 |
| Rapeseed | | | | | 2.7 | 1.1 | 14.9 | 10.1 | 5.1 | 10.9 | | 0.7 | 49.8 | |
| Soybean | | | 0.1 | 0.2 | 10.7 | 3.9 | 22.8 | 50.8 | 6.8 | 0.2 | | | | [1]2.5 |
| Sunflower | | | | | 3.7 | 5.4 | 81.3 | 9.0 | | 0.4 | | | | [1]0.5 |
| Lard | | 0.1 | 0.1 | 1.5 | 26.0 | 13.5 | 43.9 | 9.5 | 0.4 | 0.2 | 0.7 | | | [1]5-10 |
| Tallow | | | 0.1 | 3.2 | 23.4 | 18.6 | 42.6 | 2.6 | 0.7 | 0.2 | 0.3 | | | [1]5-10 |

[1]Values measure at the Analytics lab of Neste Oyj
[2]Estimation of C16-C18 FFAs in % is based on ½ * TAN (total acid number analysis), which is a fair approximation.

Typical basic structural unit of plant and fish oils and animal fats is a triglyceride. Triglyceride is an ester of glycerol with three fatty acid molecules having the structure below:

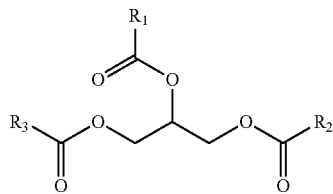

wherein $R_1$, $R_2$ and $R_3$ are same or different and represent saturated or unsaturated C3-C27 hydrocarbon chains. The length of the hydrocarbon chain for $R_x$ is typically 17 carbons and hence hydrolysis releases C18 fatty acids. Another typical length of the hydrocarbon chain for $R_x$ is 15 carbons and hence hydrolysis releases C16 fatty acids. In general, typical carbon numbers of the fatty acids linked to the two other hydroxyl groups are even, being generally between carbon chain lengths from C12 to C22.

In addition to the prevailing triglycerides, some diglycerides and monoglycerides are present as well. Diglycerides are esters of glycerol with two fatty acid molecules having alkyl group $R_x$ ($R_x$—CO—) and monoglycerides are ester of glycerol with one fatty acid molecules having alkyl group $R_x$ ($R_x$—CO—) bound to glycerol. With reference to structure above, the number of substituents R, is 1, 2 or 3. These mono- and diglycerides release glycerol in hydrolysis as well. Mono- and diglycerides are formed in minor amounts spontaneously from triglycerides during storage or under pretreatment conditions, releasing some free fatty acids. Hence, the term "triglyceride containing feedstock" refers to feed comprising mono-, di-, and triglycerides and free fatty acids.

Prior to processing, the triglyceride containing feedstock of biological origin may be pretreated with suitable known methods, such as thermally, mechanically for instance by means of shear force, chemically for instance with acids or bases, or physically with radiation, distillation, distillation/evaporation, cooling, or filtering. The purpose of chemical and physical pretreatments is to remove impurities interfering with the process or poisoning the catalysts and to reduce unwanted side reactions. Hence, according to one embodiment, the triglyceride containing feedstock is subjected to purification before entering into the hydrolysis step. This purification may include e.g. acid/water degumming, bleaching and/or deodorizing.

Thus, triglyceride containing feedstocks suitable for the process of the present invention comprise mono- di- and/or triglycerides and free fatty acids. Exemplary glyceride feedstocks are plant fats, plant oils, plant waxes, animal fats, such as lard, tallow, yellow grease, brown grease, animal oils, animal waxes, fish fats, fish oils, and fish waxes, waste and residue materials, such as used cooking oil, (UCO). Hence, preferably the triglyceride containing feedstock is selected from a group consisting of plant fats, plant oils, plant waxes, animal fats, animal oils, animal waxes, fish fats, fish oils, and fish waxes, waste and residue materials, such as UCO. Preferably, the triglyceride containing feedstock material originates from waste and/or residues of the mentioned exemplary glyceride feedstocks. More preferably, the waste and/or residues originate from sustainably-produced products, the production routes of which are traceable. Preferable feedstocks of animal origin are discussed in detail by Alm, M, (2013) Animal fats. [online]. Available at http://lipidlibrary.aocs.org/OilsFats/content.cfm?ItemNumber=40320 [Accessed 21.12.2018]. When the appropriate glyceride feedstock, optionally with pretreatment, is provided in step a., the next step, step b. cleaves the fatty acids from the glycerol backbone. Preferably, the fatty acid group may be cleaved without a chemical change to the carbon backbones.

Splitting

As used herein, splitting is used to refer to reactions releasing glycerol from glycerides. Such reactions comprise saponification, hydrolysis and transesterification of glycerides.

Saponification

Saponification is a reaction between a base, such as NaOH and triglyceride. The ester bond(s) are cleaved producing alcohols (here glycerol) and salts of carboxylic acid(s), such as Na-salts. The salts of fatty acids are acidified before they can be reacted further in the present process. Acidification transfers the salt back to acid, the fatty acid. Hence, in case of splitting conducted as saponification, said first stream obtained from step a comprises fatty acids and is subjected to phase separation of step b.

Transesterification

Transesterification is a process well known in the art, i.e. for production of biodiesels. Glycerides are reacted in the presence of an alcohol to fatty acid esters. The most common alcohol is methanol, producing fatty acid methyl esters (FAME). If ethanol is used in transesterification, fatty acid ethyl esters (FAEE) are obtained. Hence, the ester bonds between glycerol and fatty acids are cleaved releasing glycerol, but the fatty acids are still in form of esters.

Hence, in case of splitting conducted as transesterification, said first stream obtained from step a. comprises fatty acid esters and is subjected to phase separation in step b.

Hydrolysis

According to a preferred embodiment, the splitting in step a is conducted by hydrolyzing said triglyceride containing feedstock in step a. to provide a mixture comprising fatty acids, glycerol and water.

Hydrolysis in the glycerides cleaves the ester bond(s) and produces an alcohol (here glycerol) and carboxylic acid(s) (here fatty acids).

Hydrolysis can be carried out by refluxing the triglyceride containing feedstock with different catalysts. The reactions catalyzed by acid, base, or lipase are known in the art. Hydrolysis is also known to occur as an un-catalyzed reaction between fats and water dissolved in the fat phase at suitable temperatures and pressures.

A hydrolysis may be performed in a hydrolysis unit using known methods, for example such as the commercial Colgate-Emery process or modifications thereof as described in literature in the art. The hydrolysis step produces a free fatty acid stream and an aqueous glycerol stream.

According to an exemplary embodiment purified palm oil as the glyceride feedstock, is fed from the bottom of a hydrolysis column, and water is fed from the top of the column. The high temperature, such as about 250° C., and high pressure, such as about 50 MPa, enhance the solubility of water in oil phase where hydrolysis of the triglyceride containing feedstock takes place. The triglyceride containing feedstock passes as a coherent phase from the bottom to the top through the hydrolysis column tower, whereas the heavier water travels downward as a dispersed phase through the mixture of oil and fatty acids. The mixture of fatty acid and entrained water is obtained at the top while the sweet water which contains from 10 to 18% of glyceride is recovered at the bottom. Approximately two hours of reaction time is needed to reach degree of hydrolysis up to 99%. The fatty acids are discharged from the top of the hydrolysis column to an evaporator, where the entrained water is separated or flashed off. The aqueous glycerol stream is removed to prevent oxidation and degradation of the fatty acids. The water vapor is then condensed and collected at a feed water tank.

According to another embodiment, the triglyceride containing feedstock is hydrolyzed by base, such as sodium hydroxide, in a conventional manner as described in literature in the art. The process produces glycerol and salts of fatty acids. The fatty acids are liberated from the salts prior to further processing by contacting them with strong mineral acids, such as sulfuric acid. Excess sulfuric acid and the formed sodium or potassium sulfate are removed by washing with water.

According to a specific embodiment, the hydrolysis is base catalyzed, and $CO_2$ produced in the ketonisation of fatty acids according to a specific embodiment of the present invention, could be used in the neutralization of base of hydrolysis process.

The hydrolysis unit comprises equipment materials which are suitable for acidic or corrosive reagents.

The splitting provides a mixture comprising at least fatty acids, glycerol and water. It further comprises partly reacted glycerides, mono- and diglycerides as well as unreacted glycerides, which remain as triglycerides. Glycerol, water and incidental water soluble impurities form an aqueous phase, whereas mono-, di and triglycerides as well as fatty acids tend to form an oily phase, here referred to as oily phase comprising fatty acids.

Phase Separation

After cleavage of the fatty acids from the glycerol, the aqueous phase comprising glycerol may be separated from the oily phase. Hence, step b of the present process comprises subjecting said mixture comprising fatty acids, glycerol and water to a phase separation to recover an oily phase comprising fatty acids, and an aqueous phase comprising glycerol and water. The separation may be accomplished by any suitable methods known in the art including liquid-liquid extraction, supercritical solvent extraction; distillation, membrane filtration, acidulation, centrifugation, gravity separation, or combinations thereof.

Fractionation

The oily phase comprising said fatty acids is next subjected to fractionation in step c. to provide a first fatty acid fraction comprising at least 80%-wt free fatty acids having a carbon chain length of C16 or less, of the total fraction weight, and a second fatty acid fraction comprising free fatty acids having carbon number of at least C17. The first fatty acid fraction may be characterized as a light fraction, since it comprises the lightest components of the oily phase. Typically, the predominant carbon chain lengths are from C12 to C16, of which C16 is the most abundant. The first fatty acid fraction may be characterized by comprising at least 80%-wt, preferably at least 90%-wt, more preferably at least 98%-wt free fatty acids having a carbon chain length of C12-C16.

The second fatty acid fraction comprises free fatty acids having carbon number of at least C17. However, depending on the degree of the splitting, said second fatty acid fraction may in some cases be rich in glycerides, even unreacted triglycerides, which are considerably heavier. In embodiments, where the splitting, preferably hydrolysis is run practically completely, glycerides comprise di- and monoglycerides, which are present as trace amounts. Then the predominant components of the second fatty acid fraction are C18 fatty acids, saturated or unsaturated.

According to a preferred embodiment, the fractionation of step c is conducted by distillation. Distillation provides a well known and reliable method for fractionation. The fractionation step may comprise one or more distillations. Most preferably said distillation comprises at least one vacuum distillation.

The distillation conditions of step c. are guided by the characteristics of the oily phase comprising fatty acids entering said fractionation step. Distillation comprises a temperature from 200 to 300° C., preferably from 220 to 250° C. The distillation conditions of step c comprise a pressure from 0.2 to 5 kPa, preferably from 0.2 to 1 kPa.

According to an embodiment, the fractionation step c. provides two distillation cuts. The fraction comprising fatty acids having the carbon chain length between C12 and C16 is referred here as the first fatty acid fraction or light fraction comprising at least 80%-wt of free fatty acids having a carbon chain length of C16 or less. The other cut, the second fatty acid fraction or heavy fraction comprises the fatty acids having carbon chain length of C17 or more.

The separation may be realized by using at least one vacuum distillation column, preferably from two to four columns, which may be in series, depending on the accuracy needed for the separation and on the fatty acid distribution of the glyceridic feedstock, the glyceridic feedstock type and quality.

According to one exemplary embodiment of the separating of fatty acids, said separation produces
- a first fatty acid fraction wherein at least 90% of the fatty acids have a carbon chain length of less or equal to C16 i.e a fraction boiling below temperature of 365° C., preferably below 352° C., at atmospheric pressure.
- a second fatty acid fraction wherein at least 90% of the fatty acids have a carbon chain length of C17 or more, i.e. a fraction boiling above temperature of 365° C., preferably above 374° C., at atmospheric pressure, and
- a further comprising the eventual remaining glycerides i.e the distillation bottom.

The distillation temperatures are typically those measured at the exit of the distillation column(s). Herein the distillation temperatures are mathematically scaled to atmospheric pressures. In practice, conducting distillations in vacuum lowers temperatures respectively.

The non-volatile impurities in the distillation bottom can be removed using conventional methods, such as degumming and/or bleaching.

The separating can be done in a single distillation step or in two or three or more distillation steps. The distillation further purifies the distillate streams from metals and other heavy impurities which will reside after distillation at the bottom fraction. The first stream comprising fatty acids and separated from the second stream comprising glycerol by hydrolysis remain pure due to the impurities remaining in the glycerol phase. When the excess water is subsequently separated from the glycerols before hydrogenolysis the impurities will be removed along with the water phase.

Prior to hydroprocessing steps d, d' and/or e, at least one of fractions obtained may be pretreated with methods suitable for oily streams, such as those discussed in relation to pretreatment of the triglyceride containing feedstock. The chemical and physical pretreatments applied for said fractions, are especially effective, since the majority of the impurities are concentrated to the aqueous phase or to the emulsion on the interface. Hence, according to one embodiment, the first fatty acid fraction, the second fatty acid fraction or both fractions are subjected to pretreatment before entering into a hydroprocessing step. This pretreatment may include e.g. acid/water degumming, bleaching and/or deodorizing.

In an embodiment where palm oil is used as the glyceridic feedstock to the overall process for producing renewable hydrocarbon components, the fatty acid distribution after hydrolysis follows that of said glyceridic feedstock. The predominant fatty acids are oleic acid (C18:1) and palmitic acid (C16:0). Accordingly, more than 70%-wt of the total weight of the second fatty acid fraction consists of C18-fatty acids. Further, about 80%-wt of the total weight of the first fatty acid fraction consists of C16-fatty acids.

Glycerol Conversion

As considered herein, the glycerol conversion is directed to production of propanols. With "propanols" is herein referred to 1-propanol, 2-propanol or a mixture thereof. In some embodiments, is may be desirable to provide 1-propanol as the main product, with 2-propanol present only as a side product, or vice versa. Typically, a mixture of 1-propanol and 2-propanol in any proportion qualifies as a renewable propanol gasoline component and may be referred to as "propanols".

As an embodiment the present process further comprises subjecting said aqueous phase comprising glycerol and water obtained from separation of step b., to a step g. for producing propanols. Such further step contributes to the overall efficiency and feedstock utilization through recovery of propanols suitable as blend component with renewable naphtha to provide a 100% renewable gasoline. Preferably the renewable gasoline fulfils the EN 228:2012 European standard. Propanols contribute to gasoline blends as an oxygenate and additionally, provide a very good octane component, because other renewable gasoline components have typically low octanes.

Step g preferably comprises steps of
i. at least one evaporation, wherefrom the vapor phase is directed to;
ii. catalytic conversion of glycerol to 1-propanol, 2-propanol or a mixture thereof at vapor phase in presence of water,
iii. separation and recovery of 1-propanol, 2-propanol or a mixture thereof as a renewable propanol gasoline component.

Said glycerol is provided as a feed comprising glycerol and 5-90%-wt of water of the total feed weight and subjected to evaporation wherefrom a vapor phase is conducted to said catalytic conversion. Said process has been found to provide advantages. On one hand, when the amount of water in the feed exceeds that needed for the vapor phase conversion, the water remaining in the liquid phase contributes as solvent for heavy impurities present in the feed. This aqueous phase with heavy impurities therein may thus be discarded. Depending on the splitting process and the origin of the feed triglycerides, said heavy impurities vary to some degree. Typical heavy impurities present in glycerol streams or crude glycerol from transesterification comprise at least trace amounts of unconverted mono and diglycerides and water-soluble Na-soaps. The formation of these is due to the base catalyst, such as $NaOCH_4$ used in transesterification processes. In case the glycerol stream originates from hydrolysis, it may contain some mono and diglycerides or polyglycerols, i.e. glycerol polyethers. Presence of soap type impurities or phospholipids is also possible. Hence, according to an embodiment, an aqueous residue is withdrawn from the evaporation (i). Thereby, no additional purification step is needed prior to conversion. Since the evaporation provides vaporization of glycerol and some water, the heavy impurities entering the reactor with the glycerol-containing stream or the aqueous phase comprising glycerol and water are retained at least partly, preferably at least 80% by weight, more preferably at least 95% by weight of the total weight of the impurities, or even totally, in the liquid aqueous phase and do not proceed to the conversion reactor. Considering the water entering evaporation, it is divided between the vapor and liquid phases, each contributing to advantageous effects; water in vapor phase stabilized glycerol and water in the liquid phase dissolves and provides a matrix for removal of heavy impurities.

The catalytic conversion (ii) is preferably conducted at a temperature below 400° C., preferably from 200° C. to 300° C., more preferably from 230° C. to 290° C., most preferably form 250° C. to 280° C.

Hydroprocessing

The fractionated first and second fatty acid fractions are next refined to hydrocarbon components. In step d, said first fatty acid fraction is subjected either to hydroprocessing to provide paraffinic renewable aviation fuel components, or ketonisation before hydroprocessing to provide paraffinic renewable base oil, or a combination thereof. The second fatty acid fraction is subjected to hydroprocessing to provide either renewable paraffinic diesel fuel components, or renewable paraffinic technical fluid, or a combination thereof. In practice, the first or the second fatty acid fraction is subjected to one of said alternative processing steps, or if one or both of said fatty acid fractions are divided in any ratio to different processing alternatives within said steps, it is referred to as a combination thereof. These options are further discussed next.

Hydroprocessing refers to hydrodeoxygenation, hydrodesulfurization, hydrodenitrogenation, hydrodehalogenation (such as hydrodechlorination) hydrogenation of double bonds, hydrocracking, hydroisomerisation and it also removes some metals. Within the context of the present process, hydroprocessing is needed for removal of covalently bound oxygen from the fatty acid and eventual fatty acid esters, such as reminder glyceride molecules. Typically, this means deoxygenation by hydrogenation i.e. hydrodeoxygenation (HDO) and hydrogenation of double bonds.

Hydrodeoxygenation

Hydrodeoxygenation of the fatty acids may be carried out as depicted e.g. in FI100248B EP1741768A1, WO2007068795A1, WO2016062868A1 or EP2155838B1, and using a conventional hydroprocessing catalysts and hydrogen gas.

In one embodiment the hydrodeoxygenation takes place at reaction conditions comprising a temperature in the range from 100 to 500° C., preferably from 250 to 400° C., more preferably from 280-350° C., most preferably at temperature of 300-330° C.; and at a pressure in the range from 0.1 to 20 MPa, preferably from 0.2 to 8 MPa. Preferably, the weight hourly space velocity (WHSV) is in the range from 0.5 to 3.0 $h^{-1}$, more preferably from 1.0 to 2.5 $h^{-1}$, most preferably from 1.0 to 2.0 $h^{-1}$. Preferably, $H_2$ flow is in the range from 350 to 900 nl $H_2$/l feed, more preferably from 350 to 750, most preferably from 350 to 500, wherein nl $H_2$/l means normal liters of hydrogen per liter of the feed into the HDO reactor, in the presence of a hydrodeoxygenation catalyst. The hydrodeoxygenation catalyst is preferably selected from Pd, Pt, Ni, Co, Mo, Ru, Rh, W, or any combination of these, such as CoMo, NiMo, NiW, CoNiMo on a support, wherein the support is preferably alumina and/or silica.

According to an embodiment, hydroprocessing comprises hydrodeoxygenation and hydroisomerization, simultaneously or in sequence. When conducted in sequence, hydroprocessing comprises first hydrodeoxygenation and then hydroisomerization.

Isomerization (Hydroisomerization)

Isomerization can be carried out in a conventional hydroisomerization unit, such as those depicted in FI100248B, EP1741768A1, WO2007068795A1, WO2016062868A1 or EP2155838B1. Hydrogen is added into the hydroisomerization step.

Both the hydrodeoxygenation step and hydroisomerization step may be conducted in the same reactor, and even in the same reactor bed. The hydroisomerization catalyst may be a noble metal bifunctional catalyst such as a Pt containing commercial catalyst, for example Pt-SAPO or Pt-ZSM-catalyst or for example a non-noble catalyst, such as NiW. The hydrodeoxygenation and hydroisomerization steps may be performed in the same catalyst bed using e.g. the NiW catalyst in both the hydrodeoxygenation and isomerization.

The isomerization step is preferably performed at a temperature from 250 to 400° C., more preferably from 280 to 370° C., most preferably from 300 to 350° C. Pressure is preferably from 1 to 6 MPa, more preferably from 2 to 5 MPa, most preferably from 2.5 to 4.5 MPa. The WHSV is preferably from 0.5 to 3 l/h, more preferably from 0.5 to 2 l/h, most preferably from 0.5 to 1 l/h, and $H_2$ flow is in-liter $H_2$/liter feed, preferably from 100 to 800, more preferably from 200 to 650, most preferably from 350 to 500.

During isomerization n-paraffins are branched i.e. forming i-paraffins. Preferably the conditions are chosen such that the branches are located at or near the terminal ends of the molecules, and therefore the cold flow properties of renewable base oil or renewable fuels are improved.

Incidentally, the isomerization treatment is a step which predominantly serves to isomerize the hydrodeoxygenated raw material. That is, while most thermal or catalytic conversions (such as HDO) result in a minor degree of isomerization (usually less than 5 wt-%), the isomerization step which may be employed in the present process is a step which leads to a significant increase in the content of isoparaffins.

During the conventional hydroisomerization of n-paraffins to hydrocarbon components some cracking may be present. Therefore, the selection of the catalyst and optimization of reaction conditions are always important during the isomerization step. Due to cracking during isomerization renewable diesel and naphtha are formed, and may even be formed from longer carbon chain length n-paraffins such as those of renewable base oil. The renewable diesel fuel component thus obtained has typically excellent cold flow properties and can be used as winter grade diesel fuel as is i.e. 100%, without blending it to fossil middle distillate. The renewable naphtha component formed through cracking, provides a gasoline component, which when blended with the renewable propanol gasoline component obtainable from step g., provides a 100% renewable gasoline product. The renewable propanol gasoline component may be present in such a blend in an amount from 6 to 15, preferably from 6 to 12%-wt of the total weight of the gasoline.

Some of products herein provided are branched paraffinic product mixture into renewable liquefied petroleum gas (LPG) comprising C3 and C4 hydrocarbon components; renewable naphtha suitable for use as gasoline component; renewable diesel fuel and/or aviation fuel i.e. aviation fuel such as HEFA or HEFA+ components, transformer oil such as transformer oil having a boiling point of 280-300° C. or alternatively 280-350° C.; and to renewable base oil having a boiling point of 350-380° C. or 350-400° C.

According to a preferred embodiment the hydroprocessing conditions are tailored to best serve the stream in question. In practice, this may lead to the hydroprocessing conditions applied to the first fatty acid fraction in step d to differ from those applied for the second fatty acid fraction in step e.

The isomerization reaction for producing technical fluid and renewable aviation fuel is preferably conducted at temperatures at least 10° C. higher than the temperature for isomerization reaction for producing renewable diesel or renewable base oil provided that other process parameters like WHSV and pressure are similar. The most preferable isomerization reaction temperature is about 20° C. higher in the production of technical fluid and renewable aviation fuel compared to the production of renewable diesel or base oil.

As a specific embodiment, the process conditions in step d and in step e may comprise different temperatures, pressures, hydrogen to hydrogen mass ratios, WHSV or catalysts. In the step d, the isomerization is preferably carried out at 340-350° C. under 3-4 MPa pressure when HEFA is produced. In the step e, the isomerization can be carried out at a temperature 5-10° C. lower than that of step d (under the same pressure and using the same hydrocarbon to hydrogen mass ratios, WHSV and catalyst), if transformer oil is produced. In the step e, the isomerization temperature can be as low as 310-330° C. (under the same pressure and using the same hydrocarbon to hydrogen mass ratios, WHSV and catalyst) when renewable diesel is produced.

Such hydroprocessing performed to a highly homogenous fraction composition, such as a first fraction comprising at least 90%-wt, more preferably at least 98%-wt free fatty acids having a carbon chain length of C12-C16, provides a high-quality product, such as HEFA in such quality that no product distillation is needed after hydroprocessing. Mere product stabilization by removal of light volatile components, is sufficient. The same applies to base oil and technical fluid recovery.

Ketonisation

According to a preferred embodiment the process further comprises subjecting at least a part of said light fatty acid fraction to ketonisation prior to the hydroprocessing to provide a product stream of paraffinic renewable base oil.

Renewable base oil may be produced from the fatty acids, preferably from saturated fatty acids or esters containing a high content of C16 hydrocarbons. Preferably, the feed is first ketonised, then hydrodeoxygenized and/or isomerized as described for the fuel production. In the present process, the fraction subjected to ketonisation comprises saturated fatty acids or esters only. This is advantageous because the unsaturated functionalities tend to interfere with ketonisation reactions. The second fatty acid fraction comprising free fatty acids or esters having a carbon chain length of at least C17 typically rich with unsaturated functionalities, is in the present process directed elsewhere and is not a subjected to ketonisation.

Ketonisation reaction is an excellent deoxygenation reaction when deoxygenation, stability and energy density of products are the targets, as is often the case in production of fuels and base oil. Ketonisation removes 75 mol-% of the oxygen bound to carboxylic acid molecules without hydrogen. This is very important for fuel applications aiming at greenhouse gas (GHG) emission reduction. During the ketonisation reaction two fatty acid molecules are reacted together forming the corresponding linear ketone. One molecule of $CO_2$ and water is simultaneously released during the reaction.

Ketonisation reaction can be carried out with high conversion, such as 95%, or 98%, or even 99.9%, and with excellent selectivity, such as 85%, or 92%, or even 95%, which is the reason why the renewable base oil yield can be almost theoretical. Due to the very selective ketonisation reaction only few or no light hydrocarbons are formed, therefore, bio-$CO_2$ recovered from the ketonisation reaction can be very pure, preferably at least 99% by volume, and it can be used for varying applications. Naturally, the ketones produced from the free fatty acid fractions obtained by the process of the present invention may also be used as chemicals for various applications other than base oil or fuel component production.

Ketonisation conditions are typically specified by the reactor temperature and pressure, the used catalyst, the carrier gas/feed ratio and weight hourly space velocity of the feed. The selected ranges may be combined according to need depending on the parameters to be optimized.

In the present invention, the ketonisation reaction may be carried out at a reaction temperature ranging from 100 to 500° C., preferably from 300 to 400° C., more preferably from 330 to 370° C., most preferably from 340 to 360° C. The pressure range may be from atmospheric pressure to 10 MPa, preferably from 0.5 to 3.0 Mpa, more preferably from 1.0 to 2.5 MPa, most preferably from 1.5 to 2.0 MPa, in the presence of a ketonisation catalyst. A suitable ketonisation catalyst comprises one or more metal oxide catalysts, preferably the metal of the metal oxide catalyst is selected from one or more of Na, Mg, K, Sc, Fe, Co, Ni, Cu, Zn, Sr, Y, Zr, Mo, Rh, Cd, Sn, La, Pb, Bi, Ti, Mn, Mg, Ca, Zr and rare earth metals, more preferably from Ti, Mn, Mg, K, Ca, and Zr containing metal oxide catalysts, most preferably $TiO_2$. More preferably, the ketonisation catalyst is a metal oxide catalyst selected from the list consisting of one or more of: Ti, Mn, Mg, Ca, and Zr containing metal oxide catalyst. Most preferably, the catalyst is Ti containing metal oxide catalyst, such as $K_2O/TiO_2$ catalyst, or $TiO_2$ containing catalyst, such as $TiO_2$ catalyst. The weight hourly space velocity (WHSV) may be in the range from 0.25 to 3.0 h−1, preferably from 0.5 to 2.0 h−1, more preferably from 1.0 to 1.5 h−1. Ketonisation reaction may be performed in the presence of a gas in the range from 0.1 to 1.5 gas/feed ratio (w/w), preferably from 0.25 to 1.0, most preferably from 0.5 to 0.75, wherein the gas/feed ratio (w/w) means the mass of gas fed into the ketonisation reactor per the inlet fatty acid mass of the liquid feed into the ketonisation reactor. The gas is selected from one or more of: $CO_2$, $H_2$, $N_2$, $CH_4$, $H_2O$. A particular gas is $H_2$, which may advantageously flow through the reactor into the next phase also requiring the presence of hydrogen, such as HDO. The most preferred gas is $CO_2$ as this is the product gas and may be efficiently recycled back to the feed, and it provides the most selective ketonisation reaction.

According to the embodiment comprising renewable base oil production through ketonisation step, the following hydroprocessing are preferably adapted to this particular stream. Preferably hydroprocessing is conducted as hydrodeoxygenation and isomerization, either as a sequence or together in one step. It may be desirable to reduce the severity of the isomerization reaction to avoid or to reduce the amount of cracking of the renewable base oil product by selecting suitable combinations from the temperature, pressure WHSV and $H_2$ flow ranges of temperature from 250 to 400° C.; pressure is from 1 to 6 Mpa; the WHSV is from 0.5 to 3 1/h; and $H_2$ flow in-liter $H_2$/liter feed from 100 to 800.

Recovery of Renewable Hydrocarbon Components as Products

The recovery of hydrocarbon components from said first and second product streams yields components selected from renewable paraffinic base oil, renewable paraffinic diesel fuel components, renewable paraffinic naphtha components, renewable paraffinic aviation fuel components, and renewable paraffinic technical fluid. Preferably the present process provides combined renewable transformer oil and fuel production. According to another preferred embodiment, recovery of hydrocarbon components comprises recovery of at least three of components above.

The renewable content may be determined from both the starting materials and the products, by isotopic distribution involving $^{14}C$, $^{13}C$ and/or $^{12}C$ as described in ASTM D6866.

With respect to the term "renewable" in the context of a renewable fuel component, such as renewable fuels, renewable transformer oil and renewable base oil, this term refers to mixtures of organic compounds derived from any renewable source (i.e. not from any fossil based source). Such component is characterised by mandatorily having a higher content of $^{14}C$ isotopes than similar components derived from fossil sources. Said higher content of $^{14}C$ isotopes is an inherent feature characterizing the renewable fuel component and distinguishing it from fossil fuels.

Any material of biological origin means material having about 100%-wt renewable (i.e. contemporary or biobased or biogenic) carbon, $^{14}C$, content which may be determined using radiocarbon analysis by the isotopic distribution involving $^{14}C$, $^{13}C$ and/or $^{12}C$ as described in ASTM D6866 (2018).

An embodiment enables the use of the present process for combined production of at least two high value products selected from renewable base oil, renewable paraffinic transformer oil and renewable paraffinic aviation fuel (HEFA). It is seen beneficial for the HEFA product to fractionate out the heaviest components from the renewable feed material, whereas it is needed to remove the light components from transformer oil product to ensure safety in terms of adequate high flash point. In an embodiment, the production capacity of the transformer oil and HEFA may be adjusted by the selection of the process conditions and glyceride feedstock.

In an embodiment, the low temperature performance of the transformer oil and/or the HEFA product may be improved by adjusting the isomerization conditions and thereby the isoparaffin content of HEFA product.

The renewable paraffinic aviation fuel component, hydroprocessed esters and fatty acids (HEFA) consists essentially of paraffinic hydrocarbons having carbon chain length from C6 to C17, fulfilling the ASTM D7566-16b, Annex A2 specification, having a density of less than 772 kg/m$^3$ as measured according to ASTM 4052, and a freezing point of less than −40° C. as measured according to IP529.

The renewable paraffinic transformer oil consists essentially of paraffinic hydrocarbons fulfilling the IEC 60296 specification, and having viscosity at 40° C. as measured according to ENISO 3104 of 12 mm$^2$/s or below, typically 3.4 mm$^2$/s, viscosity at −30° C. as measured according to ENISO 3104 of 1800 mm$^2$/s or below, typically 42.2 mm$^2$/s, a flash point (PM) as measured according to ENISO 2719 of at least 135° C., typically 138.5° C., and acidity of less than 0.01 mg KOH/g, typically less than 0.001 mg KOH/g.

In addition to transformer oil the hydroprocessed products from the second fatty acid fraction may be use e.g. as insulating oil, heat transfer media, metal working fluid, electric vehicle (EV) battery coolant, shock absorber fluid or switch gear oil.

The present process may be utilized for producing at least one product selected from
  renewable base oil fulfilling the API Group III base oil specifications having ≥90 wt % saturated hydrocarbons, ≤0.03 wt-% sulfur and a viscosity index of ≥120;
  renewable paraffinic aviation fuel component consisting essentially of paraffinic hydrocarbons having carbon chain length from C6 to C17, fulfilling the ASTM D7566-16b, Annex A2 specification, having a density of less than 772 kg/m$^3$ as measured according to ASTM 4052, and a freezing point of less than −40° C. as measured according to IP529;
  renewable transformer oil consisting essentially of paraffinic hydrocarbons fulfilling the IEC 60296 specification, and having viscosity at 40° C. as measured according to ENISO 3104 of 12 mm$^2$/s or below, typically 3.4 mm$^2$/s, viscosity at −30° C. as measured according to ENISO 3104 of 1800 mm$^2$/s or below, typically 42.2 mm$^2$/s, a flash point (PM) as measured according to ENISO 2719 of at least 135° C., typically 138.5° C., and acidity of less than 0.01 mg KOH/g, typically less than 0.001 mg KOH/g;
  renewable diesel fuel consisting essentially of paraffinic hydrocarbons fulfilling the EN 15940:2016 European standard;
  renewable gasoline.

Detailed Description of the Process Steps and Streams Thereof

The process for producing renewable hydrocarbon components from triglyceride containing feedstock is now described with reference to FIG. 1 outlining schematically a basic flow of the process. The triglyceride containing feedstock is subjected to splitting in step a. The degree of splitting can be controlled to steer the product distribution. When splitting is conducted as hydrolysis, stream 100 comprises a mixture of at least fatty acids, glycerol and water, and some mono-, di- and triglycerides. This mixture comprising fatty acids, glycerol and water is next subjected to a phase separation step b. to recover an oily phase comprising fatty acids 101. Aqueous phase is not shown in FIG. 1.

The oily phase comprising fatty acids is fractionated in step c. to provide a first fatty acid fraction 102 or 102' comprising at least 80%-wt of free fatty acids having a carbon chain length of C16 or less, of the total first fatty acid fraction weight. Said first fatty acid fraction is in step d. subjected to either hydroprocessing, to provide paraffinic renewable aviation fuel components 103 of recovered from step f as stream 104, or subjected to ketonisation before hydroprocessing (d', including both ketonisation and hydroprocessing) to provide paraffinic renewable base oil 103, which are recovered as stream 104'. According to a specific embodiment, the first fatty acid fraction is divided between streams 102 or 102' producing eventually products 104 and 104'.

A second fatty acid fraction recovered from step c. as stream 105 or 105', comprises free fatty acids having a carbon chain length of at least C17. In step e. said second fatty acid fraction is subjected to hydroprocessing to provide renewable paraffinic diesel fuel components 106, which are recovered in step f providing stream 107. In step e' the second fatty acid fraction is subjected to hydroprocessing to provide renewable paraffinic technical fluid in stream 106', which are recovered in step f. as stream 107'.

The fractionation before the hydroprocessing enables selecting the hydroprocessing conditions for both step d and step e specifically to fit the characteristics of streams 102, 102', 105 and 105' respectively. Such hydroprocessing produces products, which do not require fractionation to recover the product as distillate, but may be recovered as bottoms product after simple removal of lightest components. The present process provides possibilities first to steer the process through the degree of splitting and again through selection of one of the two routes, step d. or step d' or a combination thereof.

Figure 2:
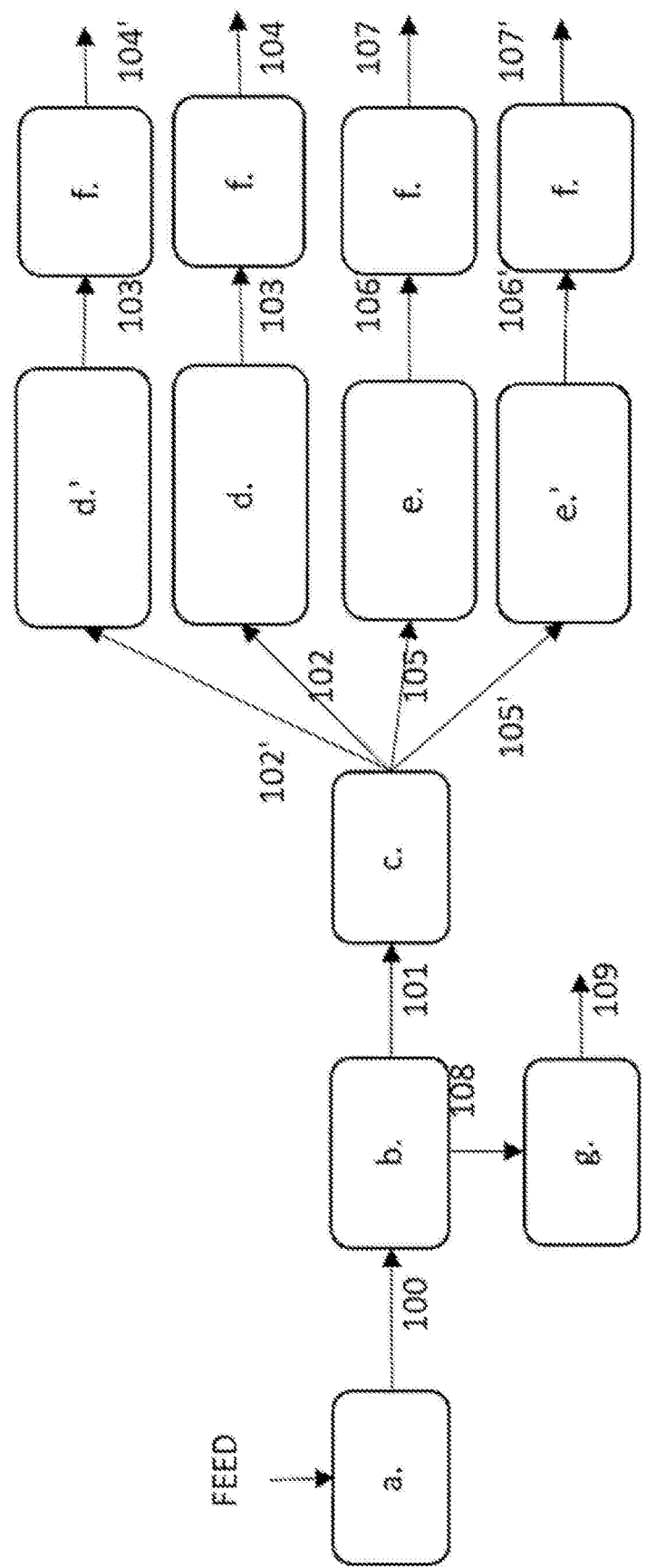
FIG. 2 shows the steps of an embodiment of the present process including the conversion of the glycerol containing stream with references to process steps claimed.

FIG. 2 provides a schematic process flow otherwise identical to FIG. 1, but providing outline for an aqueous phase comprising glycerol and water obtained in phase separation step b and led as stream 108 to aqueous phase processing in step g. Even though not shown in detail in FIG. 2, step g preferably comprises at least one evaporation, wherefrom the vapor phase is directed to catalytic conversion of glycerol to 1-propanol, 2-propanol or a mixture thereof at vapor phase in presence of water and finally separation and recovery of 1-propanol, 2-propanol or a mixture thereof in stream 109 as a renewable propanol gasoline component.

EMBODIMENTS

Two preferred embodiments of the present process are herein disclosed to exemplify the present process. Said examples are not to be considered limiting.

A Preferred Embodiment for Hydrolysis in Part

According to a preferred embodiment of the present process for producing renewable hydrocarbon components, the triglyceride containing feedstock comprises animal oils and fats. This feedstock provides a preferable fatty acid composition, rich in C16 and C18 fatty acids.

In the process the hydrolysis of said triglyceride containing feedstock is run only partly, to provide a mixture comprising the hydrolysis products, fatty acids, glycerol, water and in addition tri-, di- and monoglycerides from the original feedstock.

In phase recovery step, the aqueous phase comprising mixture of glycerol and water is separated from the oily phase. The oily phase comprises 55 wt.-% free fatty acids, 30 wt.-% triglycerides, 14 wt.-% diglycerides and 1 wt.-% monoglycerides (analyzed using the AOCS Official Method Cd 22-91). The oily phase comprising fatty acids released from the triglyceride containing feedstock, and in addition some tri-, di- and monoglycerides from the original feedstock is next fractionated at a distillation column at conditions such as 240° C. and under 0.3 kPa pressure (measured at the top of the column).

The first fatty acid fraction recovered comprises mainly ≤C16 free fatty acids (analyzed using the method ISO15304M) and is obtained as the distillate. It comprises palmitic acid (C16) in amount of 80-90%-wt of the total first fatty acid fraction weight. Yield of the distillate is 15 wt.-% of the oily phase weight. Hence, the fractionation step divides the oily phase into fractions of which the first practically consists of C16 fatty acids, hence palmitic acid.

The second fatty acid fraction comprises fatty acids of longer carbon chains, mainly ≥C17 free fatty acids, and mono-, di- and triglycerides, in practice as the bottom product. Typically, it contains a significant amount of C18 fatty acids, which may be saturated of unsaturated depending on the triglyceride source. The second fatty acid fraction recovered from said distillation as the fractionation step amounts 85 wt.-% of the total oily phase weight.

For processing the first fatty acid fraction comprising palmitic acid, there are two relevant options. At least a part or all of the first fatty acid fraction can be subjected to ketonisation, wherein two C16 fatty acids are reacted to C31 ketones providing advantageous carbon chain lengthening. These C31 ketones are then hydrodeoxygenated and optionally isomerized to provide paraffinic renewable base oil.

The other option for processing said first fatty acid fraction or a part thereof is subjecting it to hydrodeoxygenation, isomerization or a combination thereof. Selecting hydrodeoxygenation and/or isomerization conditions to this specific feed of palmitic acid, very high-quality paraffinic renewable aviation fuel can be produced and recovered therefrom. The homogeneity of the first fatty acid fraction as feed enables steering the especially the isomerization conditions to directly produce renewable aviation fuel fulfilling ASTM D7566-16b, Annex A2 specification after simple stabilization and avoiding separate product distillation.

Independently from the choices made with regard to the first fatty acid fraction, the second fatty acid fraction is subjected to hydrodeoxygenation, isomerization or a combination thereof. Again, processing this fraction separated from the original triglyceride and at least partly hydrolysed feed enables selecting the hydrodeoxygenation and/or isomerization conditions to fit this specific feed and to provide a second product stream of paraffinic renewable hydrocarbon components, wherefrom preferably high-quality paraffinic renewable diesel fuel may be recovered. Optionally, renewable paraffinic technical fluid, such as renewable transformer oil according to IEC 60296 specification may be recovered. As understood, in this embodiment, where the hydrolysis is run only partly, the second fatty acid fraction is relatively larger in volume compared to cases, where hydrolysis is more complete.

A Preferred Embodiment for Substantially Complete Hydrolysis

According to another preferred embodiment of the present process for producing renewable hydrocarbon components, the triglyceride containing feedstock is palm oil. This feedstock provides a preferable fatty acid composition to maximize production of renewable base oil or renewable aviation fuel component, rich in C16 fatty acids.

In the process the hydrolysis of said triglyceride containing feedstock is run to conversion of over 90%, to provide a mixture essentially consisting of the hydrolysis products, fatty acids, glycerol, water with only a couple of percent of tri-, di- and monoglycerides from the original triglyceride containing feedstock remaining.

In phase recovery step, the aqueous phase comprising mixture of glycerol and water is separated from the oily phase. The composition of oily phase was analyzed using a AOCS Official Method Cd 22-91, and found to comprise 92 wt.-% free fatty acids, 5 wt.-% triglycerides, 2 wt.-% diglycerides and 1 wt.-% monoglycerides.

The next step if fractionation of the oily phase comprising fatty acids by a distillation producing one distillate and a bottom product. The distillation column was operated within temperature range from 220° C. to 250° C., about at 235° C. and under 0.2 to 1 MPa, such as about 0.3 MPa pressure.

The first fatty acid fraction recovered comprises mainly ≤C16 free fatty acids (analyzed using a method ISO15304M) containing stream is obtained as the distillate. The main component therein, palmitic acid is present of amount of 80-90%-wt the total first fraction weight. Hence, the fractionation step divides the oily phase into fractions of which the first practically consists of ≤C16 fatty acids, hence typically palmitic acid.

The second fatty acid fraction comprises fatty acids of longer carbon chains, mainly ≥C17 free fatty acids, and mono-, di- and triglycerides, in practice as the bottom product. Typically, it contains a significant amount of C18 fatty acids, which may be saturated of unsaturated depending on the triglyceride source. The bottom product recovered from said distillation amounts 60 wt.-% of the total oily phase weight.

In this embodiment, where the hydrolysis is run as completely as feasible, nearly all the C16 fatty acids originating from the hydrolysis of the triglyceride containing feedstock are practically completely recovered in the first fatty acid fraction, and only traces remain bound to glycerol and thereby left to the second fraction as glycerides. Yield of the distillate is 40 wt.-% of the oily phase weight. Hence, the recovery of C16 fatty acids is relatively larger in volume compared to cases, where hydrolysis is run only partly.

For processing the first fatty acid fraction comprising palmitic acid, there are two relevant options: it may be used for the production of renewable aviation fuel or alternatively for the production of renewable base oil. At least a part or all of the first fatty acid fraction can be subjected to ketonisation, wherein two C16 fatty acids are reacted to C31 ketones providing advantageous carbon chain lengthening.

These C31 ketones are then hydrodeoxygenated and optionally isomerized to provide paraffinic renewable base oil.

The other option for processing said first fatty acid fraction or a part thereof is subjecting it to hydrodeoxygenation, isomerization or a combination thereof directly following fractionation. Selecting hydrodeoxygenation and/or isomerization conditions to this specific feed of palmitic acid, very high-quality paraffinic renewable aviation fuel can be produced and recovered therefrom. The homogeneity of the first fatty acid fraction as feed enables steering the especially the isomerization conditions to directly produce renewable aviation fuel fulfilling specifications ASTM D7566-16b, Annex A2 specification after simple stabilization and avoiding separate product distillation.

Independently from the choices made with regard to the first fatty acid fraction, the second fatty acid fraction is subjected to hydrodeoxygenation, isomerization or a combination thereof. In this embodiment processing this second fraction, which now is relatively homogenous comprising as the major part the C18 fatty acids, enables selecting the conditions to provide optimal hydrodeoxygenation, and/or isomerization conditions to fit this feed. Therefrom is provided paraffinic renewable hydrocarbon components, from which at least high-quality paraffinic renewable diesel fuel may be recovered. Another renewable product obtainable from this fraction is processing it to renewable transformer oil according to according to IEC 60296 specification.

The invention claimed is:

1. A process for producing renewable hydrocarbon components from triglyceride containing feedstock, said process comprising:
   a. hydrolyzing said triglyceride containing feedstock to provide a mixture containing fatty acids, glycerol and water;
   b. subjecting said mixture containing fatty acids, glycerol and water to a phase separation to recover an oily phase containing fatty acids, and an aqueous phase containing glycerol and water;
   c. subjecting said oily phase containing fatty acids to fractionation to provide a first fatty acid fraction containing at least 80%-wt of free fatty acids having a carbon chain length of C16 or less, of a total fraction weight, and a second fatty acid fraction containing free fatty acids having a carbon chain length of at least C17;
   d. subjecting said first fatty acid fraction to:
      hydroprocessing to provide a paraffinic renewable aviation fuel component, wherein hydroprocessing comprises hydrodeoxygenation and hydroisomerization, simultaneously or in sequence, or
      ketonisation before hydroprocessing to provide a paraffinic renewable base oil, or
      a combination thereof;
   e. subjecting said second fatty acid fraction to hydroprocessing, wherein hydroprocessing comprises hydrodeoxygenation and hydroisomerization, simultaneously or in sequence, to provide:
      a renewable paraffinic diesel fuel component,
      a renewable paraffinic technical fluid, or
      a combination thereof;
   f. recovering renewable hydrocarbon components, comprising renewable aviation fuel component and/or paraffinic renewable base oil, and a renewable paraffinic diesel fuel component and/or a renewable paraffinic technical fluid, as products from steps d and e; and
   subjecting said aqueous phase containing glycerol and water obtained from separation of step b, to a step g for producing propanols,
   wherein hydroprocessing conditions applied to the first fatty acid fraction in step d differ from hydroprocessing conditions applied to the second fatty acid fraction in step e.

2. A process according to claim 1, wherein the fractionation of step c is conducted by distillation.

3. A process according to claim 2, wherein distillation conditions of step c include a temperature from 200 to 300° C.

4. A process according to claim 2, wherein distillation conditions of step c include a pressure from 0.2 to 5 kPa.

5. A process according to claim 1, wherein the triglyceride containing feedstock is selected from the group consisting of plant fats, plant oils, plant waxes, animal fats, animal oils, animal waxes, fish fats, fish oils, fish waxes, waste and residue materials.

6. A process according to claim 5, wherein the triglyceride containing feedstock comprises:
   palm oil waste materials, animal fat waste materials or a combination thereof.

7. A process according to claim 1, wherein hydrodeoxygenation conditions comprise:
   a temperature in a range from 100 to 500° C.; a pressure in the range from 2-8 MPa; optionally a WHSV in the range from 0.5 to 3 $h^{-1}$; a $H_2$ flow of 350-900 nl $H_2$/l feed; and the hydrodeoxygenation catalyst is selected from Pd, Pt, Ni, CoMo, NiMo, NiW, CoNiMo on a support, wherein the support is alumina and/or silica.

8. A process according to claim 1, wherein hydroisomerization conditions comprise:
   a temperature in range from 200 to 450° C.; a pressure in range from 1-6 MPa; optionally a WHSV in range from 0.5-3 $h^{-1}$, and a $H_2$ flow of 100-800 nl $H_2$/l feed, in a presence of an hydroisomerization catalyst selected from a Group VIII metal, Pd, Pt or Ni; and a molecular sieve, on an alumina and/or silica support.

9. A process according to claim 1, wherein ketonisation reaction conditions comprise:
   a temperature from 300 to 400° C. and a pressure from 0.5 to 3.0 MPa, in a presence of a metal oxide ketonisation catalyst selected from one or more of Ti, Mn, Mg, K, Ca, and Zr containing metal oxide catalysts.

10. A process according to claim 9, wherein the ketonisation reaction conditions comprise:
    a presence of $CO_2$ gas flow, of a 0.1 to 1.5 gas/feed ratio (w/w).

11. A process according to claim 1, wherein the recovering of hydrocarbon components comprises:
    recovering at least three components selected from renewable paraffinic base oil, renewable paraffinic diesel fuel component, renewable paraffinic aviation fuel component, renewable paraffinic naphtha component and renewable paraffinic technical fluid.

12. A process according to claim 1, wherein step g comprises:
    i. at least one evaporation, wherein the evaporation results in a vapor phase;
    ii. catalytic conversion of glycerol to 1-propanol, 2-propanol or a mixture thereof at vapor phase in presence of water, and
    iii. separation and recovery of 1-propanol, 2-propanol or a mixture thereof as a renewable propanol gasoline component.

13. A process according to claim 12, wherein the catalytic conversion (ii) is conducted at a temperature below 400° C.

14. A process according to claim 12, wherein an aqueous residue is withdrawn from the evaporation (i).

15. A process according to claim 1, comprising:
blending the obtained propanols or renewable propanol gasoline component with a renewable paraffinic naphtha component.

16. A process according to claim 1, wherein the renewable paraffinic aviation fuel component consists essentially of:
paraffinic hydrocarbons having carbon chain length from C6 to C17, fulfilling the ASTM D7566-18 standard specification, having a density of less than 772 kg/m$^3$ as measured according to ASTM 4052D, and a freezing point of less than −40° C. as measured according to IP529.

17. A process according to claim 11, wherein the renewable paraffinic technical fluid oil is a transformer oil which consists essentially of:
paraffinic hydrocarbons fulfilling the IEC 60296 standard, and having viscosity at 40° C. as measured according to ENISO 3104 of 12 mm$^2$/s or below, viscosity at −30° C. as measured according to ENISO 3104 of 1800 mm$^2$/s or below, a flash point (PM) as measured according to ENISO 2719 of at least 135° C., and acidity of less than 0.01 mg KOH/g.

18. A process according to claim 1, for producing at least one product selected from
renewable base oil fulfilling the API Group III base oil specifications having ≥90 wt % saturated hydrocarbons, ≤0.03 wt-% sulfur and a viscosity index of ≥120;
renewable aviation fuel component consisting of paraffinic hydrocarbons having carbon chain length from C6 to C17, fulfilling the ASTM D7566-16b, Annex A2 specification, having a density of less than 772 kg/m$^3$ as measured according to ASTM 4052, and a freezing point of less than −40° C. as measured according to IP529;
renewable transformer oil consisting of paraffinic hydrocarbons fulfilling the IEC 60296 specification, and having viscosity at 40° C. as measured according to ENISO 3104 of 12 mm$^2$/s or below, viscosity at −30° C. as measured according to ENISO 3104 of 1800 mm$^2$/s or below, a flash point (PM) as measured according to ENISO 2719 of at least 135° C., and acidity of less than 0.01 mg KOH/g;
renewable diesel fuel consisting of paraffinic hydrocarbons fulfilling the EN 15940:2016 European standard; and/or
renewable gasoline fuel.

19. A process according to claim 18, comprising: producing a combined renewable transformer oil and fuel.

20. A process according to claim 2, wherein distillation conditions of step c include a temperature from 220 to 250° C.

21. A process according to claim 2, wherein distillation conditions of step c include a pressure from 0.2 to 1 kPa.

22. A process according to claim 1, wherein hydrodeoxygenation conditions comprise:
a temperature in range from 250 to 400° C.; a pressure in the range from 1-2.5 MPa; optionally a WHSV in the range from 0.5 to 3 h$^{-1}$; a H$_2$ flow of 350-900 nl H$_2$/l feed; and the hydrodeoxygenation catalyst is selected from Pd, Pt, Ni, CoMo, NiMo, NiW, CoNiMo on a support, wherein the support is alumina and/or silica.

23. A process according to claim 1, wherein hydroisomerization conditions comprise:
a temperature in range from 250 to 400° C.; a pressure in range from 2-5 MPa; optionally a WHSV in range from 0.5-3 h$^{-1}$, and a H$_2$ flow of 100-800 nl H$_2$/l feed, in a presence of an hydroisomerization catalyst selected from a Group VIII metal, Pd, Pt or Ni; and a molecular sieve, on an alumina and/or silica support.

24. A process according to claim 1, further comprising
prior to step d, subjecting the first fatty acid fraction and/or the second fatty acid fraction to pretreatment of at least one of acid/water degumming, bleaching and deodorizing.

25. A process according to claim 1, wherein the first fatty acid fraction contains at least 90%-wt of free fatty acids having a carbon chain length of C12 to C16, of the total fraction weight.

26. A process according to claim 1, wherein the second fatty acid fraction contains at least 90%-wt of free fatty acids having a carbon chain length of C17 or more, of the total fraction weight.

27. A process according to claim 1, wherein step d comprises ketonisation and step e excludes ketonisation.

28. A process according to claim 1, wherein the method is free of a separation step subsequent to step c).

29. A process according to claim 2, wherein the distillation comprises at least one vacuum distillation.

30. A process according to claim 1, wherein in the step e, the hydroisomerization is carried out at a temperature that is 5-10° C. lower than that of the step d.

* * * * *